United States Patent
Price

(10) Patent No.: US 8,790,234 B2
(45) Date of Patent: Jul. 29, 2014

(54) BRACHYTHERAPY SYSTEM AND IN VIVO DOSE DETECTOR THEREFOR

(76) Inventor: Robert A. Price, London (GB)

( * ) Notice: Subject to any disclaimer, the term of this patent is extended or adjusted under 35 U.S.C. 154(b) by 1460 days.

(21) Appl. No.: 12/374,212

(22) PCT Filed: Jul. 17, 2007

(86) PCT No.: PCT/GB2007/002692
§ 371 (c)(1),
(2), (4) Date: Dec. 31, 2009

(87) PCT Pub. No.: WO2008/009917
PCT Pub. Date: Jan. 24, 2008

(65) Prior Publication Data
US 2010/0152521 A1    Jun. 17, 2010

(30) Foreign Application Priority Data
Jul. 17, 2006   (GB) .................................. 0614211.1

(51) Int. Cl.
*A61M 36/00*    (2006.01)
(52) U.S. Cl.
USPC ............................................................ 600/7

(58) Field of Classification Search
USPC ........................................................ 600/1–8
See application file for complete search history.

(56) References Cited

FOREIGN PATENT DOCUMENTS

| DE | 41 43 401 A1 | 8/1993 |
| EP | 0 513 836 A1 | 11/1992 |
| WO | WO-03/062855 A | 7/2003 |
| WO | WO-2005/046794 A | 5/2005 |
| WO | WO-2007/067445 A | 6/2007 |

OTHER PUBLICATIONS

European Patent Office, PCT Application No. GB2007/002692 International Search Report (Apr. 15, 2008).
European Patent Office, PCT Application No. GB2007/002692 Written Opinion (Apr. 15, 2008).

*Primary Examiner* — Christine Matthews

(57) ABSTRACT

An in-vivo dose detector (41) for an HDR brachytherapy system (1; 31), wherein the detector is insertable into and movable through a catheter (15), and comprises a sensor (53) operable to detect radiation from a source (52) used to irradiate a tissue to be treated (9) in the course of an HDR brachytherapy treatment. A brachytherapy system and a method of dose monitoring are also disclosed.

13 Claims, 6 Drawing Sheets

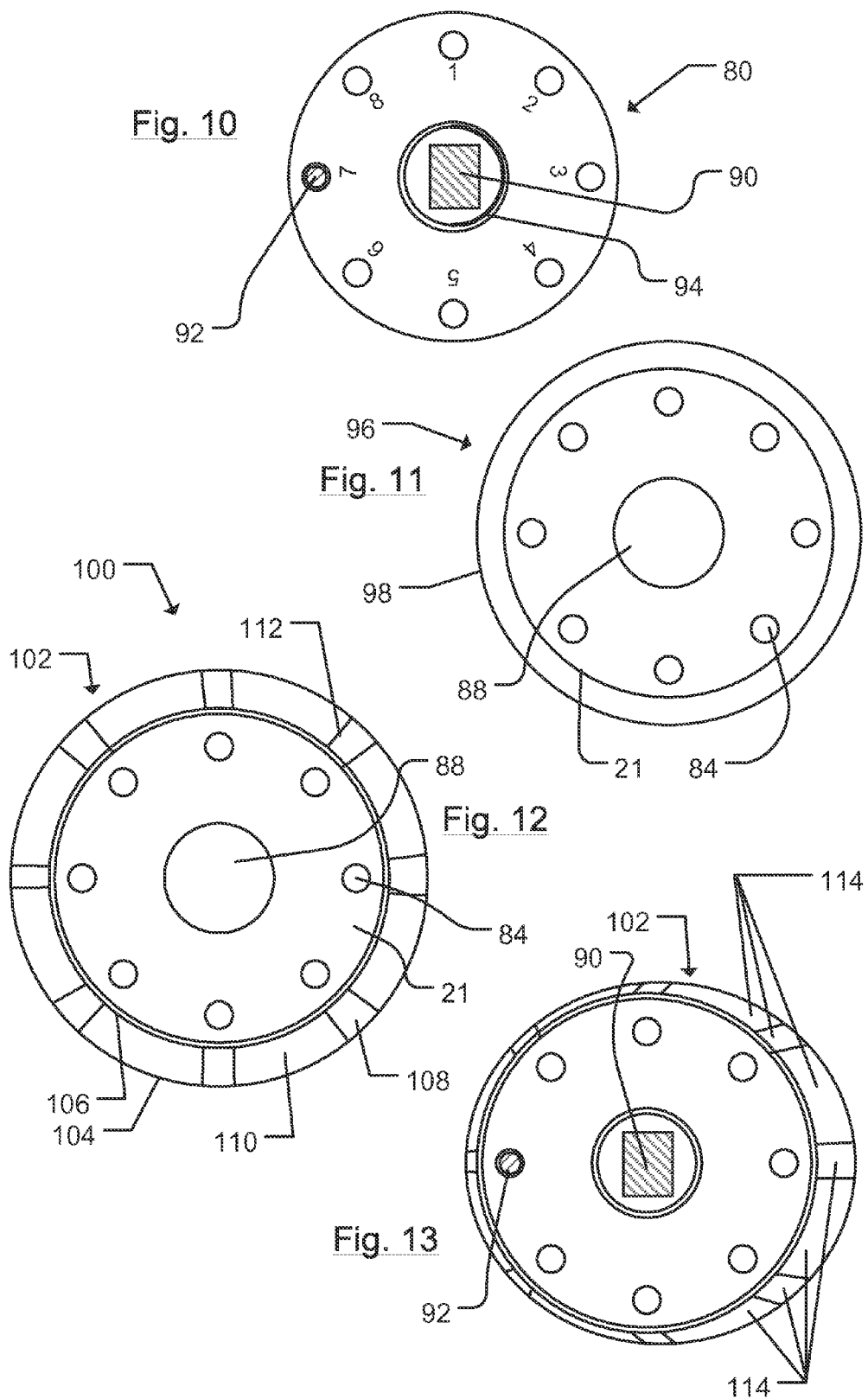

BRACHYTHERAPY SYSTEM AND IN VIVO DOSE DETECTOR THEREFOR

FIELD OF THE INVENTION

This invention relates to brachytherapy treatment systems, particularly but not exclusively to high dose rate brachytherapy treatment systems. Other particularly preferred embodiments of the present invention relate to in vivo dose detectors for such systems.

Illustrative embodiments of the present invention will hereafter be described with particular reference to high dose rate brachytherapy treatments for anal or rectal tumours. However, it will be appreciated that the teachings of the present invention are applicable to other brachytherapy treatments (such as conformal brachytherapy and pulsed-source brachytherapy for example) and to the treatment of other conditions, and as such the following detailed description should not be construed as limiting the scope of the present invention.

BACKGROUND TO THE INVENTION

Brachytherapy, as is well known in the art, is a type of radiation therapy in which radioactive materials (variously referred to hereafter as "seeds" or "sources") are placed in close proximity to, and often in direct contact with, the (typically malignant) tissue being treated. In very general terms, there are two currently practised brachytherapy treatments: low dose rate (LDR) treatments and high dose rate (HDR) treatments.

In low dose rate (LDR) treatments, sources with a relatively low radioactivity are permanently implanted within a tissue to be treated and left there to irradiate the tissue over the weeks and months following the implantation. In high dose rate (HDR) treatments, more highly radioactive sources are advanced into a tissue to be treated for a relatively short period of time, and then withdrawn from the patient once the treatment plan for that patient has been completed.

Brachytherapy treatment is appropriate for a variety of different conditions, including inter alia, prostrate tumours, breast tumours, lung cancer, oesophageal cancer, gynaecologic cancers (such as cervical cancer), anal/rectal tumours, sarcomas and head or neck cancers.

By way of illustration of the need for appropriate treatments for such conditions, in the UK over 10,000 patients per year are diagnosed with cancer of the rectum, and over 30% of the patients who have operable tumours subsequently require the use of a colostomy bag for the rest of their life.

Increasingly HDR brachytherapy is used to treat cancer of the rectum, in some instances before conventional surgical procedures are undertaken, and more recently an alternative to those surgical procedures (each of which has inherent risks associated with them). Recent studies of the use of HDR brachytherapy for the treatment of anal or rectal tumours have shown that the use of HDR brachytherapy can significantly reduce the likelihood of the patient having to be provided with a stoma.

In a commonplace HDR brachytherapy treatment (hereafter referred to simply as HDR brachytherapy), a plurality of catheters are inserted into the tissue to be treated, and a machine (known as "an afterloader") is controlled by computer to push a single relatively highly radioactive seed (for example of Iridium 192) into each of the catheters. The computer moves the seeds through the catheters in accordance with a patient treatment plan that has been carefully devised to provide an appropriate irradiation dose distribution for the tissue of the particular patient undergoing treatment. The plan defines (for each radioactive seed) a plurality of longitudinal positions within the catheter to which the seed will be moved (the so-called "dwell positions"), and the time that the seed will remain at each of those locations (the so-called "dwell time").

To implement the plan, the computer controls the afterloader to move each of the seeds to a first planned dwell position, to leave the seed at that position for the planned dwell time for that position, and then to move the source to the next planned position. This process is repeated until the dose distribution planned for treatment of the patient's tissue has been achieved.

A variety of systems have been developed to implement HDR brachytherapy, and an illustrative example of one such system is the so-called OncoSystem™ (sold by Nucletron UK Ltd (a Delft Instruments Company) of Nucletron House, Chowley Oak, Tattenhall, Chester CH3 9EX, United Kingdom). The OncoSystem™ consists of a bundle of Nucletron products for treating body-site specific cancers such as breast, rectal or gynecological cancers, and each bundle consists of OncoSmart™ applicators and disposables, and an Oncentra™ treatment control system.

The OncoSystem™ provides an accurate method of positioning sources inside the patient. However, a significant drawback of the system (and other like systems) is that measurement of the actual dose (as opposed to the planned dose) delivered to the patient is accomplished externally of the patient, and as such in a number of applications is necessarily somewhat inaccurate, principally because there is often a significant amount of tissue (often with varying radiation absorption properties) between the tumour and the skin.

The combination of technological complexity, a relatively large number of patients and the potentially hazardous nature of ionising radiation mean that there is a great potential for serious accident with potentially serious consequences if HDR brachytherapy is incorrectly delivered. To reduce, and preferably avoid, such problems—in particular damage to tissue surrounding the tumour being treated—it is important to know how much radiation is being delivered during treatment, and where that radiation is being delivered. The UK National Cancer Standard dictates that in vivo dosimetry should be performed for all types of radiation treatments, but as yet there is no effective in vivo dose measurement device available which could be used to measure how much radiation is actually being delivered during HDR Brachytherapy.

An aim of the present invention is to provide an in vivo dose detector for HDR brachytherapy, and an HDR brachytherapy system with which the detector can be used. It is anticipated that by virtue of the teachings of the present invention, it will be possible to further enhance HDR brachytherapy to the benefit of patients.

STATEMENT OF INVENTION

To this end, a presently preferred embodiment of the present invention provides an in-vivo dose detector for an HDR brachytherapy system, wherein the detector is insertable into and movable through a catheter, and comprises a sensor that is operable to detect radiation from a source used to irradiate a tissue to be treated in the course of an HDR brachytherapy treatment.

The sensor may comprise a semiconductor diode configured to operate in a photovoltaic mode without an applied voltage bias, or with an applied bias. Alternatively, the detector may comprise a MOSFET specifically constructed to be radiation sensitive, or any other two terminal device (the like of which are well known to persons skilled in the art) that is responsive to radiation.

Preferably, the sensor is coupled by a pair of wires to a set of contacts that can be connected to an electrometer or other current or voltage measuring device, the wires being encapsulated within a flexible sheath.

The sheath may include one or more locating rings that enable the position of the detector to be accurately determined. The locating rings may be of titanium or nickel. The sheath may be of polyester or nylon.

Preferably the sensor is flip-chip bonded to a substrate. The substrate may be flexible. The substrate may be in the region of 100 microns thick. The substrate may be of polyamide.

The substrate may comprise a pair of holes through which said wires extend for connection to respective contacts provided on said sensor.

Another presently preferred embodiment of the present invention provides an HDR brachytherapy system comprising: a first catheter insertable into a tissue to be treated, and through which a radioactive source can be moved by an afterloader to irradiate the tissue at one or more dwell positions set out in a treatment plan; a dose detector as described herein; a second catheter insertable into a patient for example into the tissue to be treated, and through which said dose detector may be moved to a detection position within (or in close proximity to) said tissue to be treated; and means for measuring radiation detected by the detector when the detector is in said detection position and said source is moved to said one or more dwell positions.

The system may further comprise means for determining from said treatment plan a planned dose for each said dwell position. Preferably the determining means is operable to determine from said treatment plan an integrated planned dose for all positions to which said source has been moved.

The system may comprise a comparator operable to compare a measured radiation dose to a planned radiation dose for a given dwell position, and to output a signal indicative of said comparison.

The measuring means may be operable to measure determine an integrated measured dose for all positions to which said source has been moved, the system comprising a comparator operable to compare an integrated measured dose to an integrated planned dose, and to output a signal indicative of said comparison.

The system may comprise a reporting system for receiving and storing said signal output by said comparator. The reporting system may be configured to receive patient alert criteria and activate an emergency procedure in the event that the signal output by the comparator should conflict with said patient alert criteria.

A further embodiment of the present invention relates to a method of in vivo dose monitoring in HDR brachytherapy, the method comprising: inserting a first catheter into a tissue to be treated, inserting a second catheter into the tissue to be treated, inserting a detector as herein described into said second catheter and moving said detector to a detection position within (or in close proximity to) said tissue to be treated; inserting a radioactive source into said first catheter and moving said source to one or more dwell positions set out in a treatment plan; and measuring, using said detector, the radiation emitted by said source at said one or more dwell positions.

Other presently preferred embodiments of the present invention, and features and advantages of all the embodiments described herein, are set out below in the detailed description of preferred embodiments of the present invention.

BRIEF DESCRIPTION OF THE DRAWINGS

Presently preferred embodiments of the present invention will now be described, by way of illustrative example only, with reference to the accompanying drawings, in which:

FIG. 10 is a schematic representation of a detector array in use with a probe of the type depicted in FIG. 7;

FIG. 11 is a schematic representation, in cross-section, of the proximal region of an intracavitary brachytherapy probe according to another embodiment of the present invention;

FIG. 12 is a schematic representation, again in cross-section, of the proximal region of an intracavitary brachytherapy probe according to yet another embodiment of the present invention; and FIG. 13 is a schematic illustration of the probe of FIG. 12 configured for use in a particular treatment regimen.

DETAILED DESCRIPTION OF PREFERRED EMBODIMENTS

Figure 1:
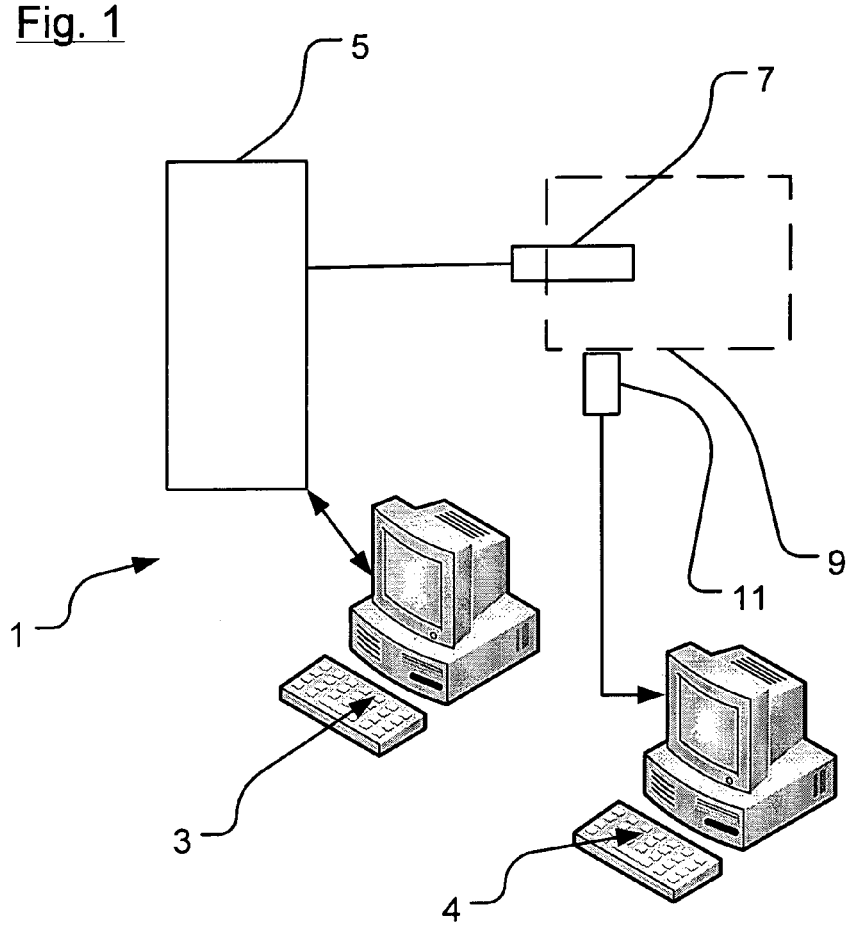
FIG. 1 is a schematic representation of a prior art HDR brachytherapy system.

Referring now to FIG. 1 of the drawings, there is shown a prior art brachytherapy system 1 which comprises a computing resource 3, in this instance a PC, and an afterloader 5 which is operable to drive a set of radioactive sources (not shown) into and out of a bundle of catheters 7 that have been inserted into the region of tissue 9 of the patient that is to be treated. Prior to the HDR brachytherapy treatment, the position of the catheters 7 in the tissue is verified by any one of a number of imaging systems, for example by means of an ultrasound or x-ray imaging system.

The computing resource 3 controls the afterloader 5 in accordance with a treatment plan that has been devised under the supervision of a physician to deliver an appropriate dose of radiation to the tissue that is to be treated by HDR brachytherapy. The treatment plan consists, for each source that is to be inserted into the patient, a list of dwell positions (longitudinal positions within a given catheter to which the source is to be advanced) and a dwell time (a period of time for which the source is stationary at each dwell position) for each of those dwell positions. The treatment plan is carefully devised to deliver an appropriate dose at each position for the tissue to be treated 9, and the deliverance of this dose is typically verified by means of a detector 11 placed outside of the patient. The detector may, as shown, be coupled to a second computing resource 4 configured to monitor and record the dose detected by the detector. As will be appreciated, without the benefit of an in vivo detector at or near to the treatment site, preparation of the treatment plan requires calculation of the dose expected at the detector (not the dose applied at the treatment site), bearing in mind the extent and composition of any intervening tissue.

Figure 2:
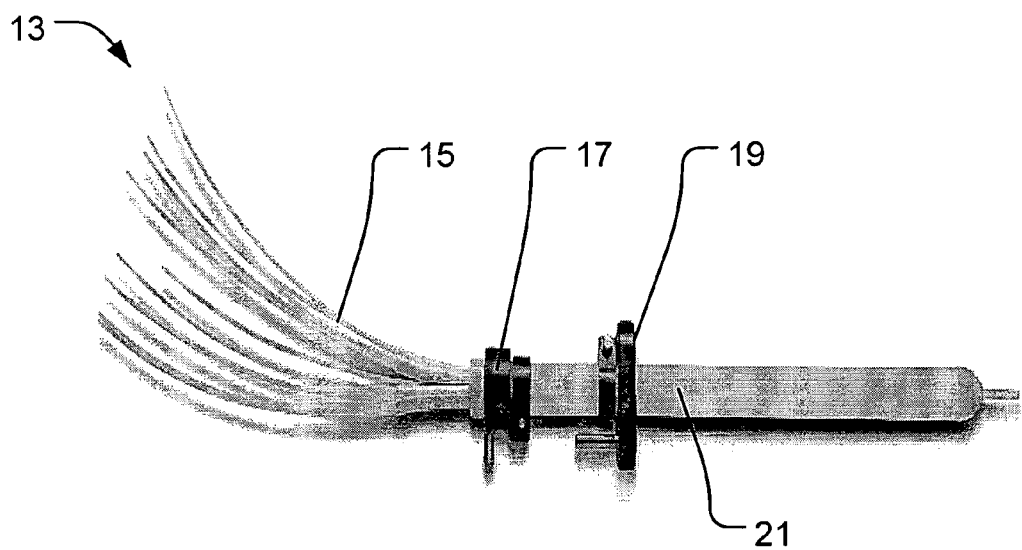
FIG. 2 is a schematic representation of an Oncosmart™ Intracavitary HDR brachytherapy rectal probe.

FIG. 2 is a schematic representation of an Oncosmart™ Intracavitary HDR brachytherapy rectal probe (available from Nucletron UK Ltd). The probe 13 consists of a plurality of catheters 15 (equivalent to the catheter bundle 7 of FIG. 1) which have been inserted into a sterile cylinder 21 which (in this instance) is to be inserted into the rectum of a patient. The catheters 15 have been fed through a numbered collar 17 which facilitates discrimination between catheters, and a support block 19 which abuts against the patient in use.

In this instance eight catheters, each of 1.2 mm in diameter, have been fitted through the collar and support into the cylinder, but a fewer or greater number of catheters may be employed if desired.

The sources, which are typically of Iridium 192, are of such a size that they can be advanced by the afterloader through the catheters, and depending on the size and shape of the tissue to be treated only a subset of the aforementioned catheters may have sources moved through them.

Figure 5:
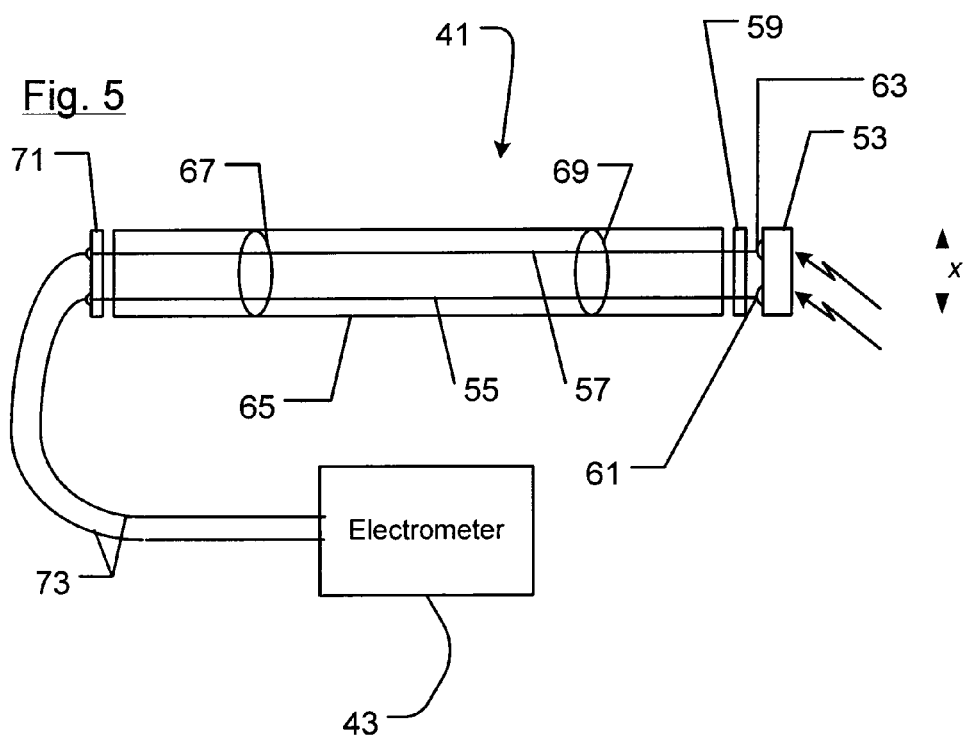
FIG. 5 is a schematic representation of a dose detector according to a preferred embodiment of the present invention.

As aforementioned, a problem with this previously proposed arrangement is that it is not possible to measure the amount of radiation delivered to the tissue being treated from within the patient, close to the sites of radiation treatment. Referring now to FIG. 5, we have addressed this problem by devising an in vivo dose detector 41 which is configured to have a dimension X that is less than the diameter of each of the catheters, and hence which can be moved into and out of the catheters, and the tissue to be treated. In the preferred arrangement dimension X is about 1 mm.

The detector comprises a sensor 53 that is operable on irradiation to generate a signal (charge or voltage, depending on the sensor) which is fed to an electrometer or other voltage or charge measuring device 43 external to the patient. The sensor 53 includes a pair of contacts 61, 63, and in other applications connectors for attachment to a substrate (such as a PCB) would extend from the contacts and be attached to the substrate so that the sensor is orientated in use with the contacts facing away from the substrate.

However, in this particular application to ensure that the detector can fit within the catheters, no connectors are provided and a pair of wires 55, 57 are instead passed through holes in a substrate 59 and directly bonded to respective contacts on the sensor. In general terms, the sensor may be said to be bonded to the substrate using over-hole flip-chip technology. The sensor may be covered by a blob of radiation permeable material (not shown) to seal the sensor within the detector.

In the preferred arrangement the substrate 59 is flexible, and may comprise a polyamide substrate that is in the order of 100 microns in thickness. The sensor may comprise a semiconductor diode configured to operate in a PV (photovoltaic) mode without an applied voltage bias, or with an applied bias. Alternatively, the detector may comprise a MOSFET specifically constructed to be radiation sensitive, or any other two terminal device (the like of which are well known to persons skilled in the art) that is responsive to radiation.

For the purposes of the following detailed description it will be assumed that the sensor consists of a semiconductor diode used in photovoltaic mode, and in this arrangement the electrometer 43 measures charge per unit time and the diode provides a linear response with respect to the applied dose. When the diode consists of a MOSFET the electrometer measures a voltage shift, and the MOSFET can either be withdrawn and interrogated once treatment has been completed or—in a preferred embodiment—interrogated in real time.

The wires 55, 57 are encapsulated within a flexible sheath 65, and terminate at a second substrate 71 which is provided with appropriate sockets (not shown) to enable the wires to be connected to the electrometer 43 via cables 73. The sheath may be of polyester or nylon and may be in the region of 30 cms in length. The wires may be enamel coated.

In a particularly preferred arrangement the sheath may include one or more (in this instance two) locating rings 67, 69 of titanium or nickel, for example, which enable the sheath to be accurately located in images derived from whatever imaging system is being used to locate the catheters in the tissue to be treated.

Although this embodiment of the invention contemplates the insertion of a single detector into a catheter, another embodiment of the invention contemplates the insertion of a plurality of detectors, each being as depicted in FIG. 5, one after the other into a catheter. In another arrangement, the detector of FIG. 5 may be modified to include a plurality of sensors arranged in a stack one behind the other with respective pairs of wires (from each sensor) encapsulated within the same flexible sheath. The sensors may be provided one immediately behind the other, or in another arrangement the sensors may be spaced from one another.

Figure 3:
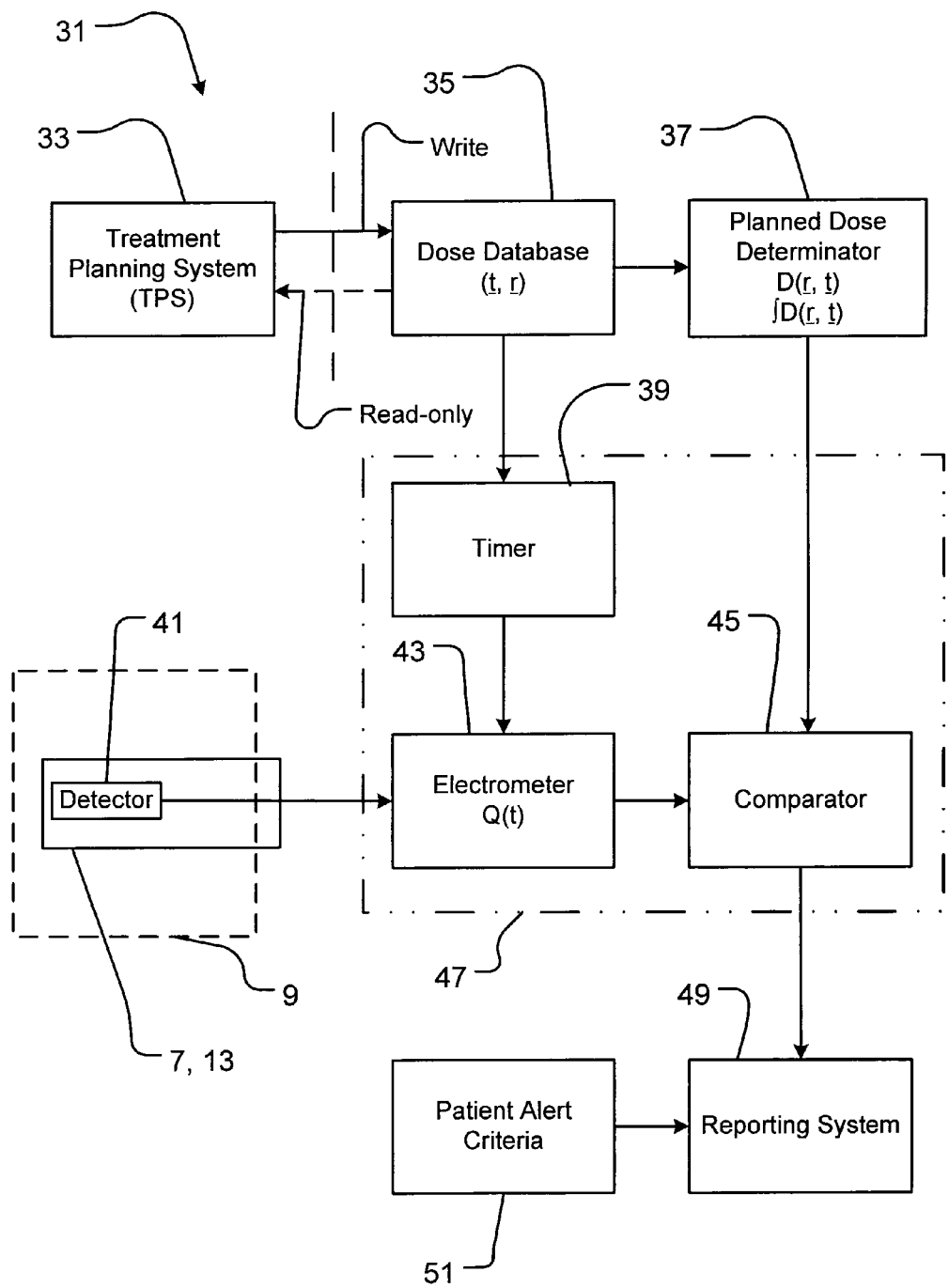
FIG. 3 is a schematic representation of an HDR brachytherapy system according to a preferred embodiment of the present invention.

FIG. 3 is a schematic representation of some of the functional components of a brachytherapy system 31 of a preferred embodiment of the present invention shown assembled for HDR brachytherapy of a tissue 9 to be treated.

As shown, a dose detector 41 has been inserted into one of the catheters 7, 13 which have been inserted into a tissue 9 to be treated. The detector of this illustrated embodiment comprises a semiconductor diode and is connected to an electrometer 43 that is configured to measure charge per unit time, and in the preferred arrangement the detector 41 remains in one known position within the tissue whilst the sources are moved relative to the detector through the catheters. As mentioned above, other types of sensor and voltage or charge measuring devices may be employed if desired.

Movement of the sources through the catheters is controlled by a known afterloader (not shown in FIG. 3) controlled by a computing resource (also not shown) in accordance with the treatment plan devised for treatment of the tissue to be treated.

The system includes a dose database 35 which interfaces with a treatment planning system 33 to load a treatment plan consisting of dwell positions "$\underline{r}$" and dwell times "$\underline{t}$" for each source that is to be employed. In the preferred embodiment, to ensure that it is not possible to overwrite or amend a given treatment plan that has been approved by a physician, the dose database 35 is configured to have read-only access to the treatment planning system.

The dose database 35 interfaces with a planned dose determinator 37 which calculates for each dwell position the planned dose $D(\underline{r}, \underline{t})$ associated with the source remaining at dwell position $\underline{r}$ for the associated dwell time $\underline{t}$. The determinator 37 is also configured to calculate the integrated patient dose $\int D(\underline{r}, \underline{t})$ which corresponds to the total dose applied to the tissue 9 thus far in the course of the HDR treatment. The dose determinator 37 is configured to output a signal representative of the planned dose for each dwell position and a signal representative of the planned integrated patient dose thus far in the HDR treatment, and in the preferred arrangement these signals are corrected for angular anisotropy caused by different detection capabilities for the sensor at different sensor/source orientations.

Figure 4:
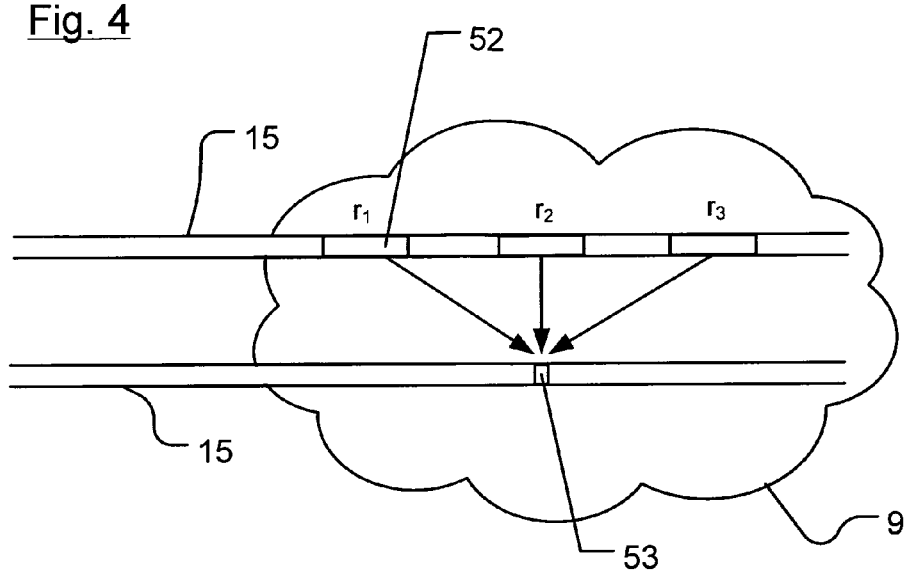
FIG. 4 is a schematic representation of a tissue undergoing treatment.

This angular anisotropy occurs because whilst the amount of radiation per unit time emitted by a source will be constant irrespective of position, the detection capabilities of the sensor typically vary in accordance with the orientation of the sensor with respect to the source. For example, if the sensor has greater detection capabilities when the radiation from the source is incident generally orthogonally to the longest faces of the sensor, and lesser detection capabilities when the radiation from the source is generally orthogonal to the shortest faces of the sensor, then the output of the sensor will vary as a source 52 is inserted into one catheter 15 and moved through positions $r_1$, $r_2$ and $r_3$ (and remains at each position for a constant dwell time t). Referring to FIG. 4, and in the particular example described above, the amount of radiation emitted by the source at each of positions $r_1$, $r_2$ and $r_3$ will be the same, but the diode will detect a greater proportion of the emitted radiation (and hence output a larger signal) when the source is at $r_1$ or $r_3$ than it will when the source is at $r_2$, and as such the planned dose (which will later be compared with the measured dose) needs to be reduced for position $r_2$ as compared to the planned doses for positions $r_1$ and $r_3$.

Referring again to FIG. 3, timing circuitry 39 is coupled to the dose database 35, and is configured to measure periods of time corresponding to the planned dwell times $\underline{t}$ at each dwell location for which the electrometer 43 measures (in this particular instance) the charge resulting from radiation detected by the detector 41. The electrometer 43, which may be any of a variety of commonly available known electrometers, outputs a signal representative of the amount of charge Q measured for a given dwell position and dwell time $\underline{t}$ to a comparator 45 which compares $Q(\underline{t})$ to $D(\underline{r}, \underline{t})$ (adjusted for angular isotropy) to determine in real time whether the actual dose for a given dwell position corresponds to the planned dose for that position. The comparator may also be configured to compare the total measured dose thus far in the procedure with the planned total dose for that stage of the procedure.

The comparator 45 outputs a signal representative of the aforementioned comparisons to a reporting system 49 that is preloaded with a set of patient alert criteria 51. These criteria define when an emergency condition is determined to have occurred, in response to which the procedure must be terminated and the sources withdrawn from the catheters. In one embodiment, the alert criteria may set dose thresholds for each dwell position which cannot be exceeded. In another embodiment, the alert criteria may be set such that the system monitors the actual dose as a function of time, and is configured such that the dose must be within a set limit, for example +/−5% Other arrangements will be apparent to persons skilled in the art.

In the event that an emergency condition is determined to have occurred, the sources are withdrawn and the procedure is terminated. Otherwise the reporting system logs the actual dose (optionally versus the planned dose) for each dwell position to provide the physician with an accurate representation of the dose at the dwell position as well as the total dose administered to the patient in the course of the treatment.

The functional components of FIG. 3 may be configured as stand-alone devices or functional software components. In an alternative arrangement one or more of these components may be integrated together. For example, in a preferred arrangement the timer, electrometer and comparator may be configured as a single application specific integrated circuit (ASIC) 47.

To ensure data integrity it is preferred, as mentioned above, that the treatment planning system is implemented by a first computing system, the controller for the afterloader is implemented by a second computing system, the reporting functionality is implemented by a third computing system and the detection functionality is implemented by a fourth computing system (communication between these systems being carefully controlled to ensure that there is no possibility of changes made in the detection or reporting system corrupting or changing data held in the HDR control system or the treatment planning system.

Whilst this is the preferred arrangement, it is of course conceivable that that the aforementioned ASIC may be integrated into a single computing resource operable to maintain the dose database, implement the dose determinator, and provide the reporting system functionality, and it is even conceivable that this computing resource may be that which is provided for control of the afterloader.

Figure 6:
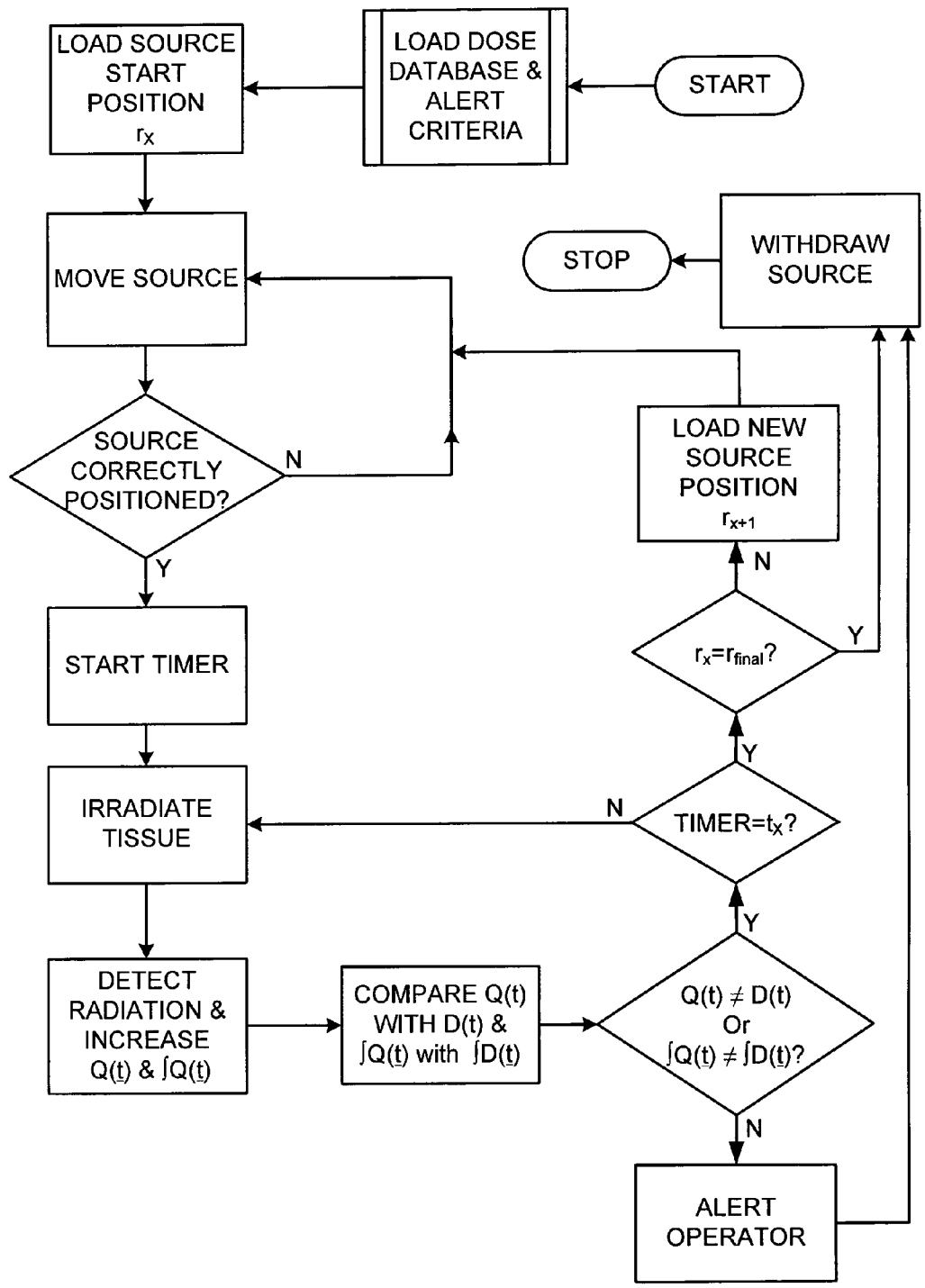
FIG. 6 is a flow diagram illustrating a mode of operation of the system.

As aforementioned, operation of the system as a whole is controlled by one or more computing resources which are in one embodiment configured to implement the method illustrated schematically in FIG. 6.

Referring now to FIG. 6, once the procedure is commenced, the dose database and alert criteria are loaded, the computing system controlling the afterloader is provided with the source start position, and the afterloader is controlled to move the source to the predetermined source start position. In the preferred arrangement the afterloader is configured to move the source relatively quickly to the first dwell position (and between subsequent dwell positions) so that only the tissue to be treated at specified dwell positions is subjected to a significant dose.

Irradiation of tissue occurs at all times once the source has been advanced into the patient, but once the source is determined to be in a given dwell position, a timer is started. Radiation emitted by the source is then detected in real time and both the charge for that position and the integrated dose for that stage of the procedure are incremented.

The detected dose for that dwell position and, optionally, the integrated dose are compared in real time with the planned dose for that position and the planned integrated dose. If either the detected dose for that position or the integrated dose should exceed the corresponding planned dose or integrated dose (determined in accordance with the alert criteria), the operator is alerted, the source is withdrawn and the procedure is terminated.

If the measured dose is less than the planned dose, it is determined whether the timer has reached the dwell time for that stage of the procedure. If the timer is less than the planned dwell time, detection of radiation is allowed to continue. If the timer is equal to the planned dwell time, the timer is reset and it is determined whether the treatment plan contains any further dwell positions. If the treatment plan does contain further dwell positions, the next source position is loaded and the procedure repeated. If the final dwell position has been reached, the source is withdrawn and the procedure is terminated.

As aforementioned, the measured and planned doses are stored in the reporting system, and the output of this system may be formatted for use with other treatment planning and patient management software.

Figure 7:
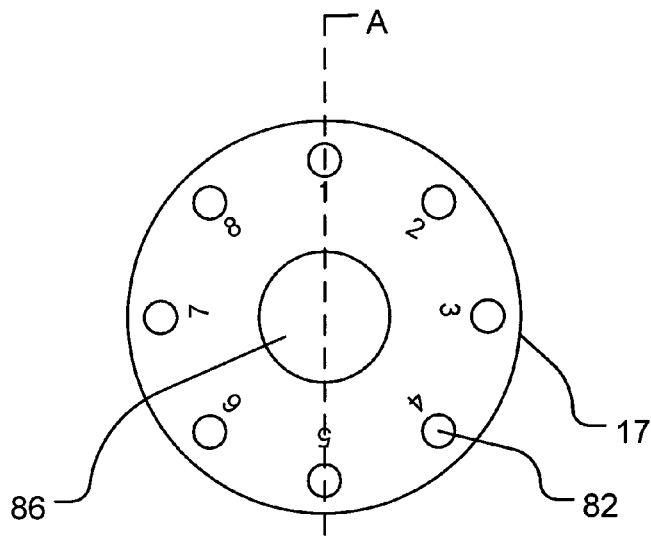
FIG. 7 is a schematic representation of the proximal end (i.e. the collar end) of an intracavitary brachytherapy probe according to an embodiment of the present invention.
Figure 8:
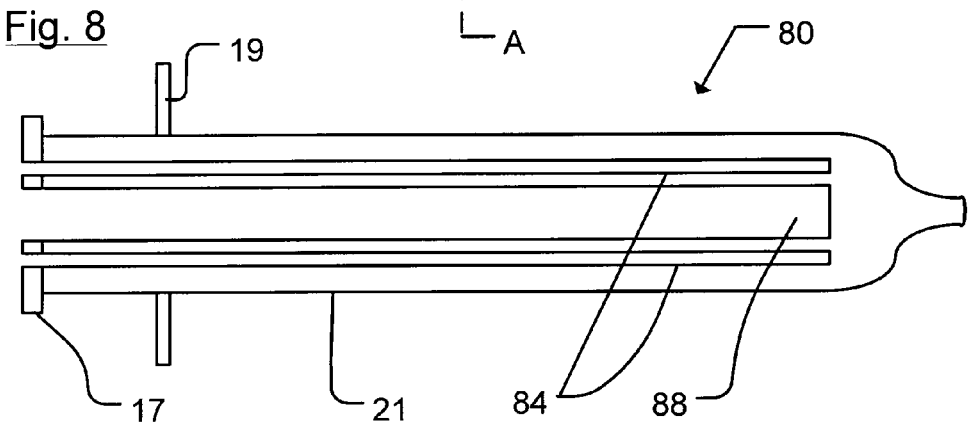
FIG. 8 is a schematic longitudinal cross-section of the probe along the line A-A in FIG. 7.

Referring now to FIGS. 7 and 8 of the accompanying drawings, there is shown an intracavitary probe 80 according to another embodiment of the present invention. FIG. 8 is a longitudinal cross-sectional view of the probe along the line A-A in FIG. 7, and FIG. 7 is a view of the probe from the proximal end thereof (i.e. a view from the end that is not inserted into the patient). The same reference numeral is used hereafter where the features of the probe shown in FIGS. 7 and 8 are the same as or similar to features of the probe shown in FIG. 2.

As with the probe of FIG. 2, the probe 80 of this embodiment comprises a sterile cylinder 21 that is coupled at one end to a collar 17 and is passed through a support block that abuts against the patient when the probe is inserted into the patient's body cavity (for example the rectum).

The collar (as before) comprises a plurality (in this instance eight) apertures 82 through one or more of which a catheter (not shown) is inserted in use. The apertures are numbered, as shown, to make it easier for an operator to discriminate between catheters. As shown in FIG. 7, the apertures 82 are arranged to register with catheter bores 84 formed within the sterile cylinder so that sources and/or detectors may be moved into and out of the probe.

The collar of this embodiment further comprises with a larger aperture 86 (in this instance a central aperture) that has a radius which is significantly larger than that of the apertures 82 through which catheters may be inserted. The larger aperture 86 registers with a larger bore 88 formed in the sterile cylinder.

The larger aperture and bore 86, 88 are provided to enable the probe to be connected to an insertion aid (such as a relatively rigid applicator) which can be used to insert the probe into the patient's body cavity. Once the probe has been inserted the insertion aid can be removed, and the larger bore 88 can then be used to accommodate a detector array, the like of which will now be described.

Figure 9:
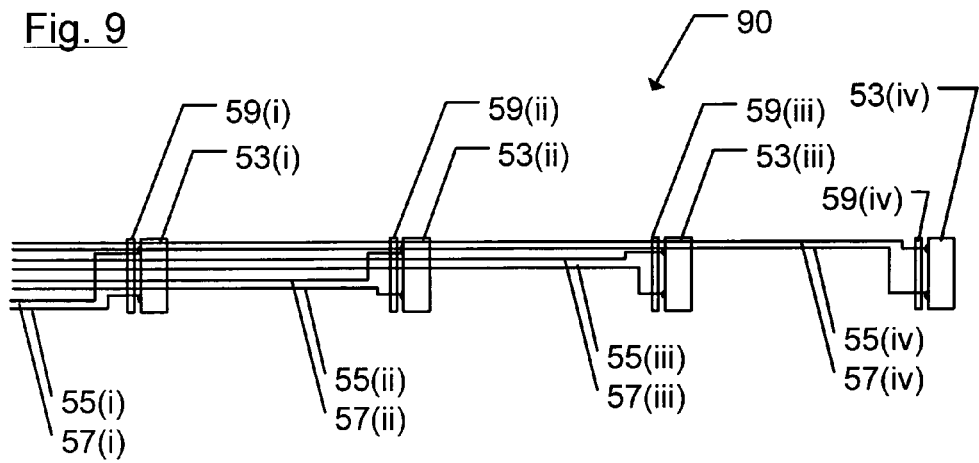
FIG. 9 is a schematic representation of a detector array for use with the probe of FIG. 7, 8, 11 or 12.

Referring now to FIG. 9, there is depicted a detector array 90 that is configured and arranged for insertion into the larger bore 88. In this illustrative example the array comprises four sensors 53(i) to 53(vi) that are each flip-chip bonded to an associated substrate 59(i) to 59(iv). The sensors may each comprise a semiconductor diode configured to operate in a PV (photovoltaic) mode without an applied voltage bias, or with an applied bias. Alternatively, the sensors may each comprise a MOSFET specifically constructed to be radiation sensitive, any other two terminal device (the like of which are well known to persons skilled in the art) that is responsive to radiation, or indeed a combination of such devices including optical (scintillation, luminescence and gel dosimeters).

In a particularly preferred arrangement the sensors each comprise a semiconductor diode used in photovoltaic mode, and in this arrangement respective pairs of terminal wires 55(i), 57(i) to 55(iv), 57(iv) connect the sensors to an electrometer (not shown in FIG. 9) that is configured to measure charge per unit time at each sensor. In such an arrangement, each diode provides a linear response with respect to the applied dose. In an alternative arrangement the sensors may each comprise a MOSFET, and in such circumstances the electrometer (not shown) is configured to measure a voltage shift. In one arrangement the MOSFETs are withdrawn and interrogated once treatment has been completed and in another particularly preferred arrangement the MOSFETs are interrogated in real time.

In the preferred arrangement the wires 55(i), 57(i) to 55(iv) to 57(iv), which may be enamel coated, are encapsulated within a flexible sheath (not shown) that may also extend around and encapsulate each of the sensors. The wires may be arranged to terminate at a second substrate (not shown) that is provided with appropriate sockets that enable the wires to be connected to the electrometer via standard cables. In the preferred arrangement the sheath is substantially transparent to radiation of interest, for example the sheath may be of polyester or nylon.

As before, it is preferred for the sheath to including one or more locating rings (not shown) of titanium or nickel, for example, which enable the sheath to be accurately located in images derived from whatever imaging system is being used to locate the catheters in the tissue to be treated.

It will be appreciated by persons skilled in the art that a greater or fewer number of sensors may be provided if desired. For example in an envisaged arrangement, ten sensors are provided.

Referring now to FIG. 10, the detector array 80 may additionally be employed to screen a part of the patient that does not need to be irradiated. For example, as shown in FIG. 10, if a particular treatment regimen required a source 92 to be advanced into and drawn out of a catheter located in catheter aperture 7, then it may be advantageous to shield patient tissue diametrically opposite the source 92 (i.e. to the right hand side of the probe as indicated in FIG. 10) from radiation. This could readily be accomplished by coating the periphery of a portion of the detector array 90, for example a portion of the sheath, with an appropriate radiation attenuating material 94.

FIG. 11 is a schematic representation, in cross-section, of the proximal region of an intracavitary brachytherapy probe 96 according to another embodiment of the present invention. In this embodiment the probe comprises an additional outer sheath 98 into which the sterile cylinder is inserted. The sheath 98 is selectively expandable, and is shown in FIG. 11 in its expanded state. Expansion of the sleeve may be accomplished by filling it with a fluid (preferably a biocompatible or inert fluid), once the probe is inserted into the patient, so as to introduce a space between the periphery of the probe and patient tissue immediately adjacent thereto. The provision of a space between the probe and the patient, as well as affecting the degree to which the patient is irradiated, also provides a gap into which one or more detectors, for example detectors of the type described above in connection with FIG. 5, may be inserted (in the preferred embodiment by passing them through catheters inserted in the gap).

FIG. 12 is a schematic representation, again in cross-section, of the proximal region of an intracavitary brachytherapy probe according to yet another embodiment of the present invention. In this embodiment the probe 100 also comprises an expandable outer sheath 102 (which sheath is shown fully expanded in FIG. 12), but in this instance the sheath is configured to have an outer layer 104 and an inner layer 106 that together define a space which is subdivided into smaller chambers 108 and larger chambers 110 by a plurality of baffles 112.

In an envisaged implementation, the smaller chambers 108 are each independently expandable and are each configured to receive a catheter (not shown), into which a detector of the type depicted in FIG. 5 may be advanced. The catheter chambers may be, as shown, generally aligned with the catheter bores in the sterile cylinder 21, or in an alternative arrangement the catheter chambers may be radially offset from the catheter bores.

In the preferred embodiment, the larger chambers 110 are also independently expandable so that neighbouring chambers can be expanded to differing degrees, thereby differentially varying the distance between the probe and the patient (i.e. so that the space between the probe and the outer sheath 102 is asymmetrical about the periphery of the probe). In a particularly preferred arrangement the larger chambers, and optionally also the smaller chambers, are configured to be capable of receiving a radiation attenuating liquid—which liquid may be used to shield a region of the patient from irradiation.

FIG. 13 is a schematic illustration of the abovementioned treatment regimen (where a source 92 is advanced into and drawn out of a catheter located in catheter aperture 7), but in this embodiment instead of shielding patient tissue diametrically opposite the source 92 by coating the periphery of a portion of the detector array 90, the expandable chambers (identified with reference numeral 114) nearest the tissue to be shielded have been filled with an appropriate radiation attenuating fluid.

As will immediately be appreciated by persons of ordinary skill in the art, the probes depicted in FIGS. 7 to 13 are eminently suitable for use with the apparatus depicted in FIG. 3, for example in accordance with the method depicted in FIG. 6.

It will also be appreciated from the foregoing that the teachings provided herein provide a detector that can be read using any conventional electrometer to provide total integrated absorbed dose, and that the system can provide integrated and time-resolved absorbed dose, and a direct measure of the absorbed dose close to the tumour site and hence a report of the difference between planned dose and delivered dose. By providing that the detector fits within existing catheters the system can readily and quickly be employed to provide in vivo dosimetry for HDR brachytherapy.

It will also be appreciated that whilst certain presently preferred embodiments of the present invention have been set out above, the scope of the present invention is not limited to those embodiments. Rather, the scope of the present invention extends to any combination of features herein described irrespective of whether that particular combination of features has been explicitly enumerated in the accompanying claims.

Skilled persons will also recognise that modifications may be made to the embodiments described above without departing from the spirit and scope of the present invention. For example, it will immediately be apparent to skilled persons that functionality described herein may be implemented in hardware, software or by means of a combination of hardware and software. It will also be apparent that whilst an electrometer is preferred, any of a variety of different devices known to persons skilled in the art may instead be employed to measure the radiation emitted.

The invention claimed is:

1. An HDR brachytherapy system comprising:
    a detector array having a plurality of detectors;
    a catheter through which a radioactive source can be moved by an afterloader to irradiate tissue at one or more dwell positions set out in a treatment plan;
    an intracavity probe, said intracavity probe comprising a holder and an outer sheath into which said holder may be inserted, wherein: said holder comprises a plurality of smaller bores into each of which said catheter may be inserted and a further larger bore into which said detector array may be inserted, the probe being configured:(i) so that said plurality of smaller bores surround said larger bore, and (ii) to hold said catheter and said detector array in a predetermined positional relationship to one another when said catheter has been inserted into at least one of said smaller bores and said detector array has been inserted into said larger bore, and wherein
    said outer sheath includes a plurality of independently expandable chambers which provide a space between the outer sheath and a peripheral surface of the holder when expanded; and
    means for measuring radiation detected by the detector array when the source is in said one or more dwell positions.

2. A system according to claim 1, comprising means for determining from said treatment plan a planned dose for each said dwell position.

3. A system according to claim 2, wherein said means for determining is operable to determine from said treatment plan an intergrated planned dose for all positions to which said source has been moved.

4. A system according to claim 2, comprising a comparator operable to compare a measured radiation dose to a planned radiation dose for a given dwell position, and to output a signal indicative of said comparison.

5. A system according to claim 3, wherein said means for measuring is operable to determine an intergrated measured dose for all positions to which said source has been moved, the system comprising a comparator operable to compare an intergrated measured dose to an intergrated planned dose, and to output a signal indicative of said comparison.

6. A system according to claim 4, comprising a reporting system for receiving and storing said signal output by said comparator.

7. A system according to claim 6, wherein said reporting system is configured to receive patient alert criteria and activate an emergency procedure if the signal output by the comparator should conflict with said patient alert criteria.

8. According to claim 1, wherein the detector array comprises a plurality of linearly arranged sensor components each coupled to a respective output, the outputs being coupled to said means for measuring radiation.

9. A system according to claim 8, wherein the sensor componets each comprise a semiconductor diode configured to operate in a photovoltaic mode with or without an applied voltage bias.

10. A system according to claim 1, wherein said smaller bores are all generally equidistant from said larger bore.

11. A system according to claim 1, wherein said smaller bores are equally anuularly located about said larger bore.

12. A system according to claim 1, wherein one or more of said chambers is configured to be expandable by injecting a liquid into said one or more chambers.

13. A system according to claim 12, wherein said liquid comprises a radiation attenuating liquid.

* * * * *